United States Patent
Auclair

(10) Patent No.: US 9,271,956 B2
(45) Date of Patent: Mar. 1, 2016

(54) COMPANION COSMETIC COMPOSITIONS

(71) Applicant: BIONOOX SUISSE SA, Cadempino (CH)

(72) Inventor: Christian Auclair, Paris (FR)

(73) Assignee: BIONOOX SUISSE SA, Manno (CH)

( * ) Notice: Subject to any disclaimer, the term of this patent is extended or adjusted under 35 U.S.C. 154(b) by 0 days.

(21) Appl. No.: 14/422,466

(22) PCT Filed: Aug. 20, 2013

(86) PCT No.: PCT/EP2013/067333
§ 371 (c)(1),
(2) Date: Feb. 19, 2015

(87) PCT Pub. No.: WO2014/029780
PCT Pub. Date: Feb. 27, 2014

(65) Prior Publication Data
US 2015/0238459 A1   Aug. 27, 2015

(30) Foreign Application Priority Data
Aug. 20, 2012  (EP) .................................... 12181058

(51) Int. Cl.
| | | |
|---|---|---|
| A61K 31/355 | (2006.01) | |
| A61K 8/34 | (2006.01) | |
| A61K 9/00 | (2006.01) | |
| A61K 47/06 | (2006.01) | |
| A61K 31/045 | (2006.01) | |
| A61K 31/352 | (2006.01) | |
| A61K 8/60 | (2006.01) | |
| A61K 8/67 | (2006.01) | |
| A61Q 19/00 | (2006.01) | |
| A61K 8/49 | (2006.01) | |

(52) U.S. Cl.
CPC ................. *A61K 31/355* (2013.01); *A61K 8/34* (2013.01); *A61K 8/498* (2013.01); *A61K 8/602* (2013.01); *A61K 8/678* (2013.01); *A61K 9/0014* (2013.01); *A61K 31/045* (2013.01); *A61K 31/352* (2013.01); *A61K 47/06* (2013.01); *A61Q 19/00* (2013.01)

(58) Field of Classification Search
CPC .................................................... A61K 31/355
USPC ......................................................... 514/458
See application file for complete search history.

(56) References Cited

U.S. PATENT DOCUMENTS

2002/0150600 A1   10/2002   Buchholz et al.
2005/0249761 A1   11/2005   Buenger et al.

FOREIGN PATENT DOCUMENTS

| EP | 1 205 177 A2 | 5/2002 |
| RU | 2 382 635 C1 | 2/2010 |
| WO | 03/051287 A2 | 6/2003 |

OTHER PUBLICATIONS

International Search Report, dated Oct. 21, 2013, from corresponding PCT application.

*Primary Examiner* — Taofiq A Solola
(74) *Attorney, Agent, or Firm* — Young & Thompson

(57) ABSTRACT

A composition includes dihydroquercetin, α-tocopherol and bisabolol. The use of the composition in a cosmetic method for limiting, alleviating and/or preventing cutaneous discomfort, especially cutaneous discomfort induced by a disease or induced by a therapy, a radiotherapy treatment and/or chemotherapy treatment, and the process of manufacturing the composition are also described.

16 Claims, No Drawings

COMPANION COSMETIC COMPOSITIONS

FIELD OF INVENTION

The present invention relates to a composition comprising dihydroquercetin, α-tocopherol and bisabolol. The invention also relates to the use of the composition of the invention in a cosmetic method for limiting, alleviating and/or preventing cutaneous discomfort, especially cutaneous discomfort induced by a disease or induced by a therapy, a radiotherapy treatment and/or chemotherapy treatment. The present invention also relates the process of manufacturing the composition of the invention.

BACKGROUND OF INVENTION

Cutaneous Discomfort Induced by Radiotherapy

Radiotherapy is a therapy applied in the treatment of various cancers, including breast head and neck cancers. It is well established that radiation may cause skin injuries, such as rash and modification of the appearance of the skin.

Dermatitis is a generic term covering various skin damages resulting from inflammation. Almost 90% of people treated with ionizing radiations will show symptoms consistent with radiation induced dermatitis. Radiation has some aggressive side effects that can affect the skin during the treatment, such as skin atrophy, erythema, dry desquamation, moist desquamation, ulceration, soreness, burning and itching. In serious reactions, skin can begin sloughing off due to the complete eradication of stem cells in the basal layer. Dermatitis resulting from overexposure to sources of radiant energy, such as X-rays, gamma or like radiation, is one of the most serious complications in the treatment of neoplastic diseases which can lead to the suspension of treatment.

Cutaneous discomfort occurring following ionizing radiation can produce a major discomfort for the patient, limit daily activities and may result in break from treatment. Cutaneous discomfort should therefore be limited or prevented.

Williams et al evaluated common methods used for preventing skin toxicity during radiotherapy (Williams M S, Burk M, Loprinzi C L, et al, Int. J. Radiat. Oncol. Biol. Phys., 1996, 36:345-349). It was especially shown that *aloe vera* had no protective effect on patients receiving breast irradiation. The administration of Biafine did not allow to evidence statistical amelioration. The use of topical steroids was reported to decrease radiation dermatitis, however, steroid may cause undesirable effects.

WO 03/051287 discloses a composition for reducing, treating or preventing at least one adverse effect of ionizing radiation by topical application, said composition comprising a mixture of at least one non-flavonoid antioxidant and at least one flavonoid and wherein at least one component is obtained from green tea. The exemplified composition of patent application WO03/05187 comprises quercetin as flavonoid and a mixture of vitamin A, vitamin E acetate, ascorbyl palmitate and lipoic acid as non-flavonoid antioxidant. The patients self-evaluated the effects of the administration of this composition and noted less severe radiation dermatitis after radiation therapy.

Cutaneous Discomfort Induced by Chemotherapy

It is also well established that skin damages may be caused by cancer chemotherapy. Treatment by tyrosine kinase inhibitors or monoclonal antibody tyrosine kinase inhibitors often provokes irritation, inflammation and cutaneous erythema.

Epidermal growth factor receptor inhibitors (EGFRI) such as cetuximab (Erbitux®), gefitinib (Iressa®) and erlotinib (Tarceva®) are used for treating colorectal, lung, head and neck cancers. Skin rash associated with chemical EGFRI therapy roughly affects more than 50% of patients receiving treatment and more than 80% of patients receiving the antibody treatment (cetuximab). The incidence of severe rash (grade 3) is reported in up to 16 to 18% of patients.

The cutaneous eruptions appear primarily on the face, neck and upper torso; the face being often the first area affected by the rash. The rash is characterized by interfollicular- and follicular-based erythematosus papules and pustules and is usually seen during the first two weeks of the therapy. It tends to wax and wane during therapy, with "flare ups" occasionally noted after infusions. Rash symptoms typically resolve without scarring within one to two months after stopping treatment.

Severe rash is usually painful and requires dose interruption of EGFRI agent, tetracycline analog treatment and application of hydrocortisone cream, clindamycin gel or pimecrolimus, plus a steroid dose pack given orally.

When chemotherapy is administered during or soon after radiation treatment, a severe skin reaction that is called radiation recall sometimes develops. It usually appears on the area of skin in the field of treatment several weeks after the end of radiotherapy. Patients develop red and tender swelling or wet peeling skin. After the skin heals, it remains discolored. Certain chemotherapy agents are more likely to lead to radiation recall than others, such as Adriamycin, actinomycin D, methotrexate, bleomycin, cyclophosphamide, 5-fluorouracil, hydroxyurea and vincristine/vinblastine.

The management of EGFRI-associated rash has attracted attention and various compositions were tested. For example, Regenecare™ gel (MPM Medical Inc. Irving Tex.) is a collagen, lidocaine and *aloe vera* based wound care gel. Kozloff et al reported that it was effective in reducing itching and pain associated with rash; 100% of patients would recommend this product to others ("*Evaluation of Regenecare™ Topical Gel in the Treatment of Skin Rash Associated with Cetuximab (Erbitux®), Tarceva® and Other EGFR Inhibitors-Treated Cancer Patients*", M. F. Kozloff, Patricia A. Gowland, Joy Vlamakis, Julie Koch, Gail Ratko, Lisa Gravitt, Diane Palmer, CCRP Ingalls Memorial Hospital, Cancer Research Center, Harvey, Ill. Kimberly Purdy Lloyd, M. S., MPM Medical Inc., Irving, Tex.). Ocvirk et al. reported the efficacy of a cream containing urea and vitamin K1 in reducing cutaneous toxicity, with a median time to improvement of 8 days (J. Ocvirk, M. Rebersek, M. Boc, T. Mesti and M. Ebert. Journal of Clinical Oncology, 2010 ASCO Annual Meeting Proceedings-Post-Meeting Edition-. Vol 28, No 15_suppl (May 20 Supplement), 2010: e14011). Lacouture et al. (J. Clin. Oncol. 2010, 28, 1351-1357) developed an pre-emptive skin treatment with topical steroid and doxycycline that didn't affect the effectiveness of the therapy (Lacouture M, Basti S, Patel J, Benson A., J Support Oncol, 2006, 4:236-238).

Cutaneous Discomfort Induced by Autoimmune and Atopic Skin Diseases

There are more than 80 known types of autoimmune diseases and some of them can provoke skin damages such as itchy skin, dry skin, and itchy skin rash. One of them, psoriasis, is a chronic inflammatory disease of the skin that cannot be cured. Psoriasis signs and symptoms can vary from person to person but may include red, dry plaques of thickened skin (that may bleed), thickened, pitted or ridged nails, itching, burning and soreness. Psoriasis commonly affects the skin of the elbows, knees, and scalp. Therapies have been developed to relieve the patient, mainly with creams and ointments. Emollient or moisturizing creams may help to reduce itching and moisturize dry skin and topical ointments may soothe the inflammation. These creams usually contain corticosteroids or retinoids alone or in combination.

Atopic skin diseases are also known as atopic dermatitis, and are one of the most common forms of eczema. This is a skin disorder that includes severe itching or burning, bleeding, oozing or crusting, and scaling skin. Therapies commonly involve atopic non-steroid cream or oral steroids for more severe symptoms.

Skin Inflammation Processes

The cellular processes of skin inflammation are regulated by a series of specific cell signals that stimulates a variety of cell types, resulting in a cascade of events including white blood cell (WBC) recruitment and activation. The physiologic response to these signals or WBC activity (or both) results in the traditional inflammatory response: the clinically observable milieu of signs and symptoms associated with tissue injury and healing.

Dermatitis inflammation is associated with increased Th2 cells in acute cell lesions. Chronic dermatitis results in the infiltration of inflammatory dendritic epidermal cells, macrophages, neutrophils, eosinophils and mast cells. IL-12 production by these various cell types results in the switch to a Th1-type cytokine milieu associated with increased IFN-γ.

At the site of the radiation injury, mast cells, platelets, nerve endings, endothelial cells, and other resident cells release signaling molecules and chemoattractants that recruit leukocytes to the affected area. Neutrophils, a type of granulocyte, are the first leukocytes to appear at the injured site.

There is an accumulation of evidences indicating that neutrophils and mast cells play a key role in the maintenance of inflammation. Neutrophils have a huge potential to directly inflict damage to tissue via the secretion of proteases and toxic oxygen metabolites, as well as driving inflammation through antigen presentation and secretion of cytokines, chemokines, prostaglandins, and leucotrienes. Neutrophils release cytokines, including interleukin (IL)-1, IL-6, tumor necrosis factor (TNF)-alpha, gamma interferon (INF-gamma) and others.

US2005/249761 relates to a topical composition for the prophylaxis and/or treatment of skin diseases and/or inflammation reactions of the skin and can also be used for the cosmetic care of the skin. This composition comprises aryl oxime and bisabolol, and may further include adjuvants and/or excipients. Aryl oximes are known to be useful for the treatment of skin inflammation but are difficult to formulate. In US patent application US2005/249761, it was shown that the use of bisabolol enables their stabilization while reinforcing the anti-inflammatory action. However, no evaluation of the efficacy of this composition is provided.

Even though skin therapies may have very impressive effects, they may induce side effects, and they do not always provide a comfortable local relief for the patient, especially in the beginning of the treatment, where the patient may still experience itching or rash.

There is thus a need to improve comfort, well-being and quality of life of patients, without adding to their pharmaceuticals intake. This invention aims at reaching this need, and relates to cosmetic compositions, suitable to be administered to patients, i.e people being treated, as "companion cosmetic compositions" or "add-on non-therapeutic compositions".

In the meaning of this invention, "companion cosmetic composition" means a cosmetic composition intended to assist patient in the management of their therapy-related cutaneous discomfort. Advantageously, companion cosmetic compositions are safe, do not contain phototoxic and/or photosensibilizing components, show no toxicity. Moreover, companion cosmetic compositions do not affect the effectiveness of the therapy.

The companion cosmetic compositions of the invention may be useful to limit and/or prevent cutaneous discomfort induced by a therapy, a radiotherapy treatment and/or chemotherapy treatment.

The composition of the present invention comprises:
dihydroquercetin (DHQ),
α-tocopherol, and
bisabolol.

Dihydroquercetin (DHQ) is the common name of 3,3',4',5,7-pentahydroxyflavone dehydrate, also called 2-(3,4-dihydroxyphenyl)-3,5,7-trihydroxy-4H-1-benzopyran-4-one dehydrate, also known as taxifolin. DHQ is a natural compound of the flavonoid family.

Flavonoids are reported to have therapeutic potentials because of their antioxidant, anti-inflammatory, anti-allergic or anti ischemic properties. Furthermore, flavonoids may penetrate into deep skin layers after topical application. Of these, quercetin is one of the most documented, but is known to be genotoxic, mutagen and with a low chemical stability.

DHQ is a valuable alternative to quercetin as it is characterized by a great chemical stability with conserved significant biological and pharmacological properties and by its safety. DHQ has been identified as a powerful antioxidant, as safe, and as a natural preservative. Therefore it has been marketed for 15-20 years as food supplement in Russia and in the US. It has also been found to inhibit both neutrophils and mast cell activation, two main events involved in the inflammatory process.

α-Tocopherol, commonly named vitamin E, has many biological functions, the antioxidant function being considered as the most important one. Furthermore, it is lipid-soluble. It performs its function as antioxidant on connection with the glutathione peroxidase pathway and it protects cell membrane from oxidation by reacting with lipid radicals produced during the lipid peroxidation chain reaction. This process would remove the reactive free radical intermediates and prevent the oxidation chain reaction from continuing. The resulting α-tocopheroxyl radicals may be converted back to the reduced form through reduction by other oxidants such as ascorbate, retinol or ubiquinol, as well as DHQ. Without willing to be bound by a theory, it is the Applicant understanding that in the composition of the present invention, α-tocopherol favors the recycling of DHQ under its active phenolic form.

Bisabolol (6-methyl-2-(4-methyl-3-cyclohexen-1-yl)-5-hepten-2-ol, or 1-methyl-4-(1,5-dimethyl-1-hydroxyhex-4(5)-nyl)cyclohexen-1) is a sesquiterpene that is found in various plants, including herbal tea and chamomile. The most important known effects of bisabolol are anti-inflammatory, wound healing, anti-bacterial, anti-mycotic and anti-phlogistic properties. Therefore it is widely used in cosmetic and personal care products. Especially, bisabolol may be used to enhance the transepidermal penetration, in other words it may be used to increase diffusivities across the modified skin barrier. In the present invention, bisabolol is used as a vehicle of DHQ and/or α-tocopherol and is thought to facilitate the diffusion of DHQ and/or α-tocopherol to the dermal area.

The composition of the invention presents the advantage to have a high stability and preservability. Moreover, the composition of the invention produces a pleasant feeling when applied on skin.

SUMMARY

The present invention relates to a composition comprising dihydroquercetin, α-tocopherol and bisabolol.

According to one embodiment, the concentration of dihydroquercetin is ranging from 0.5% to 10% w/w in weight of the total weight of the composition, preferably from 1% to 7% w/w, more preferably from 2% to 5% w/w.

According to one embodiment, the concentration of α-tocopherol is ranging from 0.05% to 5% w/w in weight of the total weight of the composition, preferably from 0.5% to 2% w/w.

According to one embodiment, the concentration of bisabolol is ranging from 0.02% to 2% w/w in weight of the total weight of the composition, and preferably ranging from 0.2% to 1% w/w.

According to one embodiment, the composition further comprises a cosmetically acceptable vehicle.

According to one embodiment, the vehicle is a cosmetically acceptable base.

According to one embodiment, the cosmetically acceptable base comprises at least one compound selected from the group comprising animal fat, vegetable fat, higher alcohols, glycols or a mixture of thereof.

According to one embodiment, the composition of the invention further comprises at least one component selected from the group comprising surfactants, pigments, stabilizers, emollients, humectants or a mixture of thereof.

According to one embodiment, the composition of the invention comprises:
  0.5% to 10% w/w in weight of the total weight of the composition of dihydroquercetin,
  0.05% to 5% w/w of α-tocopherol,
  0.02% to 2% w/w of bisabolol, and
  a cosmetically acceptable vehicle.

According to one embodiment, the composition is a cream, a gel, an ointment, a solution, an emulsion, a mask, a milk, a lotion, a serum, a paste, a foam or a suspension, and preferably a cream.

According to one embodiment, the composition is designed for topical administration.

According to one embodiment, the composition of the invention is for use as companion cosmetic composition in a method for treating and/or limiting cutaneous discomfort induced by radiotherapy treatment and/or chemotherapy treatment or induced by diseases implying cutaneous discomfort.

According to one embodiment, the composition of the invention is for use as companion cosmetic composition in a method for treating dermatitis.

According to one embodiment, the composition of the invention is for use as companion cosmetic composition in a method for treating skin inflammation.

The invention further relates to a process of manufacturing the composition of the invention, the process comprising a step of blending DHQ, α-tocopherol and bisabolol with a cosmetically acceptable vehicle.

DEFINITIONS

In the present invention, the following term has the following meaning:

"about" preceding a figure means plus or less 10% of the value of said figure.

"companion cosmetic composition" refers to a cosmetic composition characterized in that it is administered to treated people.

"discomfort" refers to the absence or to a decrease in the feeling of ease or well-being. In one embodiment, a discomfort may be related to the presence of pain.

"cosmetically acceptable" refers to a component that is suitable for use in contact with the skin without undue adverse side effects (such as toxicity, irritation, allergic response, and the like).

"vehicle" refers to a substance with which the component of interest is mixed or wherein the component of interest is dissolved. In an embodiment, the vehicle may be a cosmetically acceptable base.

"cosmetically acceptable base" refers to a cosmetically acceptable vehicle comprising a lipophilic component.

DETAILED DESCRIPTION

Composition

This invention relates to a composition comprising dihydroquercetin (DHQ), α-tocopherol and bisabolol.

In an embodiment, the concentration of DHQ in the composition of the invention is ranging from 0.5% to 10% w/w (i.e. in weight, by weight of the total composition), preferably ranging from 1% to 7% w/w, more preferably ranging from 2% to 5% w/w, more preferably about 5% w/w.

In an embodiment, the concentration in the composition of the invention of α-tocopherol is ranging from 0.05% to 5% w/w in weight by weight of the total composition, preferably ranging from 0.5% to 5% w/w, more preferably about 1% w/w.

In an embodiment, the concentration in the composition of the invention of bisabolol is ranging from 0.02% to 2% w/w in weight by weight of the total composition, preferably ranging from 0.2% to 1% w/w, more preferably about 0.5%.

According to an embodiment, the composition of the invention further comprises a cosmetically acceptable vehicle.

In an embodiment, the composition of the invention comprises 0.5% to 10% in weight of the total weight of the composition of dihydroquercetin, 0.05% to 5% w/w of α-tocopherol, 0.02% to 2% w/w of bisabolol, and a cosmetically acceptable vehicle.

In an embodiment, the composition of the invention comprises 1% to 7% in weight of the total weight of the composition of dihydroquercetin, 0.05% to 5% w/w of α-tocopherol, 0.02% to 2% w/w of bisabolol, and a cosmetically acceptable vehicle.

In an embodiment, the composition of the invention comprises 2% to 5% in weight of the total weight of the composition of dihydroquercetin, 0.5% to 5% w/w of α-tocopherol, 0.2% to 1% w/w of bisabolol, and a cosmetically acceptable vehicle.

In an embodiment, the composition of the invention comprises 5% in weight of the total weight of the composition of dihydroquercetin, 2% w/w of α-tocopherol, 1% w/w of bisabolol, and a cosmetically acceptable vehicle.

In an embodiment, the vehicle is a cosmetically acceptable base.

According to an embodiment, the cosmetically acceptable base comprises at least one compound selected from the group comprising animal fat, vegetable fat, higher alcohols, glycols, mineral oil or a mixture thereof.

In an embodiment, animal fat is for example stearic acid. In an embodiment, vegetable fat is for example linoleic acid, jojoba oil (also called oil *simmondsia chinensis*) or a mixture thereof. In an embodiment, higher alcohols are for example cetearyl alcohol. In an embodiment, glycols are for example propylene glycol. In an embodiment, mineral oil is for example paraffin oil.

According to an embodiment, composition of the invention further comprises at least one component selected from the group comprising surfactants, pigments, stabilizers, emollients, humectants or a mixture of thereof.

In an embodiment, surfactants are for example PEG-100 stearate, PEG-20 stearate or a mixture thereof. In an embodiment, stabilizers are for example carbomer. In an embodiment, pigments are for example zinc oxide. In an embodiment, emollients are for example caprylic/capric triglyceride, dicapryl ether, glyceryl stearate, glyceryl monostearate or a mixture thereof. In an embodiment, humectants are for example glycerin, sorbitol or a mixture thereof.

According to an embodiment, the composition of the invention further comprises perfume, such as for example citronellol, geraniol, limonene, or a mixture thereof.

According to an embodiment, the composition of the invention further comprises water. In a specific embodiment, the composition of the invention is an oil-in-water emulsion.

In an embodiment, the composition of the invention does not comprise any tar or sulfur derivatives such as steroids, vitamin D3 analogs, keratolytic agents, topical retinoids, artificial or genetically manipulated substances, known allergic agents, artificial coloring or scent agents.

In one embodiment, DHQ is extracted from a type of larch wood, preferably from Siberian larch.

In an embodiment, DHQ containing powder contains at least 96% w/w by weight of DHQ and corresponds to the technical requirements and sanitary rules on the basis of analytical and microbiological reports.

According to an embodiment, the composition of the invention further comprises components that are commonly employed as a cosmetic base and that are known by the skilled artisan.

In an embodiment, the composition of the invention is designed for topical administration.

According to an embodiment, the composition of the invention is under the form of a cream, a gel, an ointment, a solution, an emulsion, a mask, a milk, a lotion, a serum, a paste, a foam or a suspension. In a preferred embodiment, the composition of the invention is a cream.

In an embodiment, the composition of the invention is a cosmetic composition. In an embodiment, the composition of the invention is a pharmaceutical composition.

In an embodiment, the composition of the invention is stable over one year in standard storage conditions.

In an embodiment, the composition is stored in a container.

The present invention further relates to a kit comprising a container comprising the composition of the invention.

In an embodiment, the container is a glass container. In an embodiment, the glass container is sterilized using a dry heat sterilizer.

In an embodiment, the container is a plastic container. In an embodiment, the plastic container is sterilized using UV irradiation using low-pressure "Hard Quartz Glass" UV Lamps.

Process

The invention also relates to a process for manufacturing the composition of the invention.

In an embodiment, the process of the invention comprises a step of blending DHQ, α-tocopherol and bisabolol with a cosmetically acceptable vehicle.

In an embodiment, the process of the invention comprises a preliminary step of dissolving DHQ in jojoba oil (Oil *Simmondsia chinensis*) before blending DHQ, α-tocopherol and bisabolol with a cosmetically acceptable vehicle.

In an embodiment, the cosmetically acceptable vehicle is manufactured by any conventional method known in the art.

Use of the Composition

The invention further relates to the use of a composition according to the invention as a companion cosmetic composition in a method for treating cutaneous discomfort.

In an embodiment, the composition of the invention is for use as companion cosmetic composition in a method for treating and/or limiting cutaneous discomfort induced by radiotherapy treatment and/or chemotherapy treatment or induced by diseases implying cutaneous discomfort.

According to one embodiment, the composition of the invention is for use as companion cosmetic composition in a method for treating dermatitis.

According to one embodiment, the composition of the invention is for use as companion cosmetic composition in a method for treating skin inflammation.

In a specific embodiment, the composition of the invention is used as companion cosmetic composition in a method for treating by radiotherapy women having a breast cancer.

In an embodiment, the composition of the invention is for an external use. In an embodiment, the composition of the invention is applied on damaged and/or undamaged skin.

In an embodiment, the composition of the invention is applied to the skin before potential exposure to radiation and/or chemotherapy.

In an embodiment, the composition of the invention is applied to the skin at least once 24 h before the start of the potential radiation and/or chemotherapy exposure, and three times in the 24-hour period following the radiation and/or chemotherapy exposure.

In an embodiment, an amount of composition of the invention is applied which is sufficient to cover the afflicted area of the skin with a thin layer of the topical composition.

In an embodiment, the composition should be rubbed into the skin until little or no residue remains on the skin.

In one embodiment, the composition is applied on the skin into a regular massage.

According to an embodiment, the composition of the invention may be applied one, two, three or more times a day.

In an embodiment, the application of the composition of the invention allows the reduction or inhibition of the discomfort caused by skin irritation, inflammation, or cutaneous erythema, and preferably these resulting from anticancer radiotherapies or targeted cancer therapy treatments using tyrosine kinase inhibitors or monoclonal tyrosine kinase inhibitors, or these resulting from breast cancer radiotherapy treatment or head and neck radiotherapy treatment or any cancer radiotherapy treatment.

In an embodiment, the composition of the invention may be used to limit and/or inhibit the discomfort caused by cutaneous alterations resulting from cancer treatment by chemotherapy, especially chemotherapies using EGFRI and multikinases inhibitors, chemotherapies leading to hand and foot syndrome or other related skin toxicity.

The invention also relates to a method of relieve of cutaneous discomfort comprising topically administering the composition of the invention.

In an embodiment, the method of relieve of cutaneous discomfort is applied to women having a breast cancer, especially women having a breast cancer treated by radiotherapy or treated by chemotherapy.

In an embodiment, the method is employed to reduce or inhibit the discomfort caused by irritation, inflammation and cutaneous erythema comprising the step of applying on the skin of a patient in need thereof a composition according to the present invention.

EXAMPLES

The present invention is further illustrated by the following examples. Examples are not intended to limit the scope of the present invention.

Example 1

Skin Cream Composition

A topical composition comprising:
5% w/w DHQ
1% w/w α-tocopherol
0.5% w/w bisabolol
jojoba oil
cosmetically acceptable vehicle comprising:
  water
  paraffin oil
  cetearyl alcohol
  glyceryl monostearate
  dimethicone E 900 (silicone)
  PEG 20 stearate
  PEG 100 stearate
  cetylic alcohol (isohexadecanol)
  imidazolin urea
  butyl phenyl methylpropional
  cinnamyl alcohol
  citronellol
  geraniol
  limonene The composition of example 1 is obtained by first blending the components of the cosmetic vehicle and then by blending the vehicle with DHQ (previously dissolved in jojoba oil), α-tocopherol and bisabolol.

Example 2

Effect of Composition of Example 1 on Targeted Chemotherapy Induced Skin Inflammation Composition of example 1 was tested in a clinical trial enrolling 12 patients.

The clinical trial consisted in a placebo-controlled unblended study. In one arm, patients were treated with the composition of example 1 whereas in the control arm, patients were treated with a placebo composition containing the cosmetically acceptable vehicle of example 1. Protocol of the trial consisted in the application of the cream once a day on the injured skin area. The objective of the trial was to evaluate the treatment efficiency by the objective measurement of inflammation extent and patient self-evaluation.

All patients were treated for metastatic melanoma using kinase inhibitors.

Reporting of the trial clearly shows a significant decrease in skin inflammation in patients treated with DHQ containing composition compared to patients treated with placebo.

Patients' self-evaluation indicates a feeling of improved comfort and well-being following DHQ treatment. For self-evaluation, all patients (12 enrolled patients) should answer to the following questions:
  a) How severe is your skin pain feeling before using the composition?
  Please place a vertical mark on the line below between 0 (no pain) and 10 (severe pain)
  No pain 0_____5_____10 severe pain
  b) How severe is your skin pain feeling after using the composition?
  Please place a vertical mark on the line below between 0 (no pain) and 10 (severe pain)
  No pain 0_____5_____10 severe pain Results:

All enrolled patients have pain index >5 before using the composition comprising DHQ. All enrolled patients using the composition comprising DHQ have a pain index <5 after use.

70% of the enrolled patients treated by placebo preparation have a pain index >5 after use.

No adverse effect was observed. No allergic reaction was observed. No inflammatory potentiating effect following chemotherapy was observed.

Example 3

Effect of Composition of Example 1 on Radiotherapy Induced Skin Inflammation

Radiation therapy for breast cancer begins two to four weeks after surgery. The dose of radiations usually delivered to the entire breast is between 4500 and 5000 cGy. Booster dose of 15000 cGy is usually delivered to the tumor site. Treatment is given for five days per week during a period of six weeks.

Composition of example 1 was tested in a clinical trial enrolling 12 patients.

The clinical trial consisted in a placebo-controlled unblended study. In one arm, patients were treated with the cosmetic composition of example 1 whereas in the control arm, patients were treated with a placebo composition containing the cosmetically acceptable vehicle of example 1. Protocol of the trial consisted in the application of the cream once a day on the irradiated skin area just following the irradiation during the overall duration of the treatment. The primary objective of the trial was to evaluate the occurrence of adverse effects. The secondary objective of the trial was to evaluate the treatment efficiency by the objective measurement of inflammation extent and patient self-evaluation.

All patients included were women diagnosed for an early breast cancer undergoing radiotherapy course during five weeks. All patients put the cream or the placebo cream on the irradiated area on twice a day from day one of the treatment.

Reporting of the trial clearly shows a significant decrease in skin inflammation in patients treated with DHQ containing composition compared to patients treated with placebo.

Patients' self-evaluation indicates a feeling of improved comfort and well-being following DHQ treatment. For self-evaluation, all patients (12 enrolled patients) should answer to the following questions:
  a) How severe is your skin pain feeling before using the composition?
  Please place a vertical mark on the line below between 0 (no pain) and 10 (severe pain)
  No pain 0_____5_____10 severe pain
  b) How severe is your skin pain feeling after using the composition?

Please place a vertical mark on the line below between 0 (no pain) and 10 (severe pain)

No pain 0_____5_____10 severe pain

Results:

All enrolled patients have pain index >5 before using the composition comprising DHQ. All enrolled patients using the composition comprising DHQ have a pain index <5 after use.

70% of the enrolled patients treated by placebo preparation have a pain index >5 after use.

No adverse effect was observed. No allergic reaction was observed. No inflammatory potentiating effect following the cumulative skin irradiation was observed.

The invention claimed is:

1. A composition comprising dihydroquercetin, α-tocopherol and bisabolol.

2. The composition according to claim 1, wherein the concentration of dihydroquercetin is ranging from 0.5% to 10% w/w in weight of the total weight of the composition.

3. The composition according to claim 1, wherein the concentration of α-tocopherol is ranging from 0.05% to 5% w/w in weight of the total weight of the composition.

4. The composition according to claim 1, wherein the concentration of bisabolol is ranging from 0.02% to 2% w/w in weight of the total weight of the composition.

5. The composition according to claim 1, wherein said composition further comprises a cosmetically acceptable vehicle.

6. The composition according to claim 1, wherein said composition further comprises a cosmetically acceptable base.

7. The composition according to claim 1, wherein said composition further comprises a cosmetically acceptable base comprising at least one compound selected from the group comprising animal fat, vegetable fat, higher alcohols, glycols or a mixture of thereof.

8. The composition according to claim 1, further comprising at least one component selected from the group comprising surfactants, pigments, stabilizers, emollients, humectants or a mixture of thereof.

9. The composition according to claim 1, comprising
   0.5% to 10% w/w in weight of the total weight of the composition of dihydroquercetin,
   0.05% to 5% w/w of α-tocopherol,
   0.02% to 2% w/w of bisabolol, and
   a cosmetically acceptable vehicle.

10. The composition according to claim 1, wherein the composition is a cream, a gel, an ointment, a solution, an emulsion, a mask, a milk, a lotion, a serum, a paste, a foam or a suspension, and preferably a cream.

11. The composition according to claim 1, wherein said composition is designed for topical administration.

12. A method for treating cutaneous discomfort, wherein said method comprises administering a companion cosmetic composition comprising dihydroquercetin, α-tocopherol and bisabolol.

13. The method according to claim 12, for treating and/or limiting cutaneous discomfort induced by radiotherapy treatment and/or chemotherapy treatment or induced by diseases implying cutaneous discomfort.

14. The method claim 12, for treating dermatitis.

15. The method claim 12 for treating skin inflammation.

16. Process of manufacturing a composition comprising dihydroquercetin, α-tocopherol and bisabolol, the process comprising a step of blending DHQ, α-tocopherol and bisabolol with a cosmetically acceptable vehicle.

\* \* \* \* \*